US00PP33632P2

(12) United States Plant Patent
Hansen

(10) Patent No.: US PP33,632 P2
(45) Date of Patent: Nov. 9, 2021

(54) ***SEDUM* PLANT NAMED 'BACK IN BLACK'**

(50) Latin Name: ***Sedum* hybrid**
Varietal Denomination: Back in Black

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,220

(22) Filed: Apr. 16, 2021

(51) Int. Cl.
*A01H 5/12* (2018.01)
*A01H 6/32* (2018.01)

(52) U.S. Cl.
USPC ..... Plt./479
CPC ..... *A01H 6/328* (2018.05)

(58) Field of Classification Search
USPC ..... Plt./479
CPC ..... A01H 6/328
See application file for complete search history.

*Primary Examiner* — Anne Marie Grunberg

(57) ABSTRACT

A new and distinct ornamental perennial *Sedum* plant named 'Back in Black' is characterized by tight-forming upright mounds with dark greyed-purple glaucous foliage that resists powdery mildew and subsequent scaring. The numerous, dark, greyed-purple stems are highly branched and resist lodging in summer heat and rains. Individual flowers of light-pink with deep garnet carpels completely covering the top of the plant. The new plant is useful for the landscape in containers, as specimens or en masse.

1 Drawing Sheet

Botanical designation: *Sedum* hybrid.
Cultivar denomination: 'Back in Black'.

STATEMENT REGARDING PRIOR DISCLOSURES UNDER 37 CFR 1.77(B)(6)

The claimed plant was first sold privately to Plant Delights Nursery on May 4, 2020 by Walters Gardens, Inc., who obtained the plant and all information relating thereto, from the inventor. Subsequently the new plant was also sold privately to Willoway Nurseries, Inc., Prides Corner Farms and Overdevest Nurseries, LP. No plants of *Sedum* 'Back in Black' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Sedum* plant, botanically known as *Sedum* and hereinafter referred to by the cultivar name 'Back in Black'. There are over 300 recognized species of the genus *Sedum*.

The new *Sedum* plant is a selection of a planned breeding program conducted by the inventor, at a wholesale perennial nursery in Zeeland, Mich., USA.

The new *Sedum* plant was selected as a single seedling from a self-pollination of a proprietary, unreleased, unnamed hybrid known only by the breeder code 14-30-1 on Sep. 1, 2015 at a wholesale perennial nursery in Zeeland, Mich. *Sedum* 'Back in Black' was assigned the breeder code number 15-19-4 to keep it separated from among thousands of other seedlings of this and other crosses when it progressed through the initial trial phase in the fall of 2016. The selected single seedling clone was originally selected for it strong, healthy, dense growth, colorful foliage and flowers and intermediate traits between the two parents.

Asexual reproduction of *Sedum* 'Back in Black' by division at a wholesale perennial nursery in Zeeland, Mich., USA since October of 2016 and subsequent vegetative shoot tip cuttings has shown that the unique features of this new *Sedum* plant are stable and reproduced true to type in successive generations.

SUMMARY OF THE INVENTION

Plants of *Sedum* 'Back in Black' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of *Sedum* 'Back in Black' and distinguish it as a new and distinct autumn stonecrop plant unique from all other autumn stonecrop plants known to the inventor:

1. Tight-forming upright mounds with vertical stems.
2. Center stems remain erect throughout the growing season producing full habit.
3. Glaucous, dark, grey-purple foliage resists powdery mildew and the subsequent scaring.
4. Numerous, dark greyed-purple stems produce dense flower clusters of light-pink with deep garnet carpels completely cover the top of the plant.

In comparison with the parent, the new plant has a larger width and height and retains its upright stems better through the entire growing season. The nearest comparison varieties known to the inventor are: 'Karl Funkenstein' (not patented), 'Black Jack' U.S. Plant Pat. No. 16,736, 'Night Embers' U.S. Plant Pat. No. 29,211, 'Touchdown Teak' U.S. Plant Pat. No. 26,078, 'Dark Magic' U.S. Plant Pat. No. 27,619 and 'Desert Black' U.S. Plant Pat. No. 24,902. 'Karl Funkenstein' is less full in habit and smaller foliage size, the leaves are less greyed and the flower petals are deeper reddish. 'Black Jack' is not as greyed-purple and is more prone to powdery mildew. 'Night Embers' has foliage that is less glaucous and more glossy. 'Touchdown Teak', 'Dark Magic' and 'Desert Black' are all smaller in habit with smaller leaves that are less glaucous greyed-purple with thinner stems and less dense flowering. The female and male parent was not as stocky and full in habit, and tended to lodge late in the season.

BRIEF DESCRIPTION OF THE PHOTOGRAPHS

The photograph of the new plant demonstrates the unique traits and the overall appearance of *Sedum* 'Back in Black'. The colors are as accurate as reasonably possible with color reproductions of this type. Variations in ambient light spectrum, source and direction may cause the appearance of minor variation in color. The plants used in the photograph were three-year-old plants grown in an open, full-sun trial garden at a wholesale perennial nursery in Zeeland, Mich. with supplemental water and fertilizer when needed. No plant growth regulators or pinching have been used.

DETAILED BOTANICAL DESCRIPTION

Figure 1:
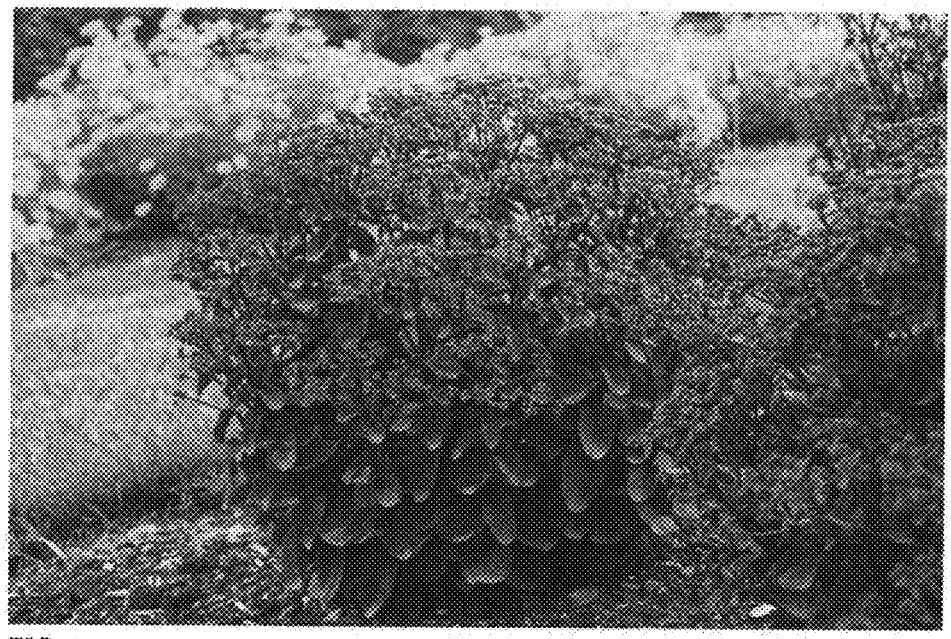
FIG. 1 shows the habit of the new plant with foliage in early stages of flowering.
Figure 2:
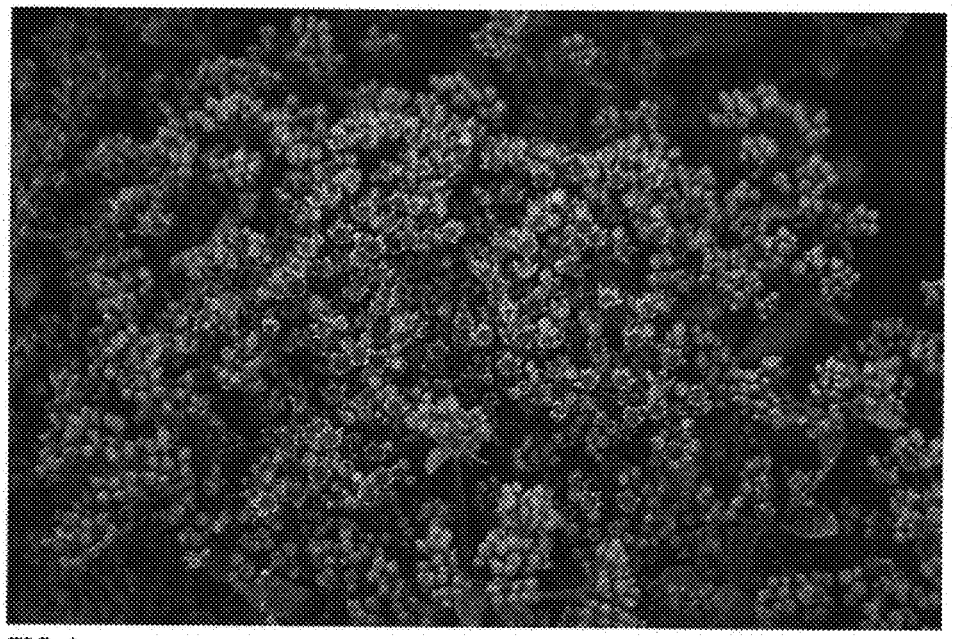
FIG. 2 shows a close-up of the flowers and buds of the new plant in mid-summer.

The following is a detailed description of three-year-old plants of the new cultivar as grown outdoors in a full sun trial plot at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Botanical designation: *Sedum* hybrid;

Cultivar denomination: 'Back in Black';

Parentage: A self-pollination selection of the unreleased, unnamed proprietary hybrid known only by the breeder code 14-30-1;

Asexual propagation: Stem tip cuttings and division;

Time to initiate roots: About two weeks;

Time to finish a 3.8 liter flowering container: About three months in the summer from a rooted 2.5 cm plug;

Root description: Thick, fleshy; freely branching; creamy white to light tan in color;

Plant habit: Winter-hardy herbaceous perennial; upright mound; stiff upright stems; dense and full, not opening in center later in the season; flower heads freely branching;

Growth rate: Moderately vigorous;

Plant size: About 52.0 cm tall and 70.0 cm wide in full flower;

Stems: Terete; glaucous; glabrous; diameter at base to about 15.0 mm, average about 12.0 mm; heavily branched in distal portion; about 10.0 cm long from base to initial branches; about 14 stems per plant and 10 branches per stem;

Stem color: Proximally or in shade nearest RHS 147C, distally nearest RHS N187A;

Lateral branches: To about 10 per stem; glaucous; glabrous; terete; primary branches to about 30.0 cm long and about 6.0 mm diameter at base;

Lateral branch color: Nearest RHS N187A;

Foliage: Ovate to obovate; spirally arranged; simple; smooth; sarcous; glabrous and glaucous on both surfaces; sessile; thick; apex bluntly acute to rounded; base attenuate; margin irregularly and shallowly dentate, 6 to 7 teeth in distal two-thirds of leaf; teeth about 3.0 mm to 8.5 mm apart; decreasing in size distally; attitude outward; about 34 per stem;

Foliage size: To about 9.6 cm long, 6.0 cm across and 4.0 mm thick; average about 6.2 cm long, 4.9 cm across and 3.0 mm thick; decreasing distally;

Foliage color: Adaxial young nearest RHS 189B blushed with nearest RHS N187C, abaxial young RHS 189B; mature adaxial nearest RHS N187A and abaxial between RHS 191A and RHS N138C variably blushed with nearest RHS N187A;

Petiole: Leaves sessile;

Venation: Palmate, barely distinguishable; slightly raised abaxial;

Vein color: Adaxial midrib nearest RHS N187A and abaxial midrib between RHS 191A and RHS N138C; secondary veins not obvious;

Flower: Stellate, actinomophic; pentamerous; persistent; attitude upright to outwardly in terminal compound cymes; size about 8.0 mm across and 7.0 mm deep;

Flower number: About 200 to 275 per branch and 1,000 to 1,500 flowers per stem and 8,000 to 25,000 per plant;

Fragrance: None detected;

Flowering season: Beginning mid-summer in Zeeland, Mich. for about three weeks;

Longevity: Flower cymes remain effective for about three weeks on the plant and one week as cut flowers; individual flowers and calyces persistent and effective for about three weeks;

Flower buds about one day prior to opening: Ellipsoidal; apex acute; base truncate; about 5.0 mm long and about 3.0 mm diameter near middle;

Flower bud color: Nearest RHS NN155A, moderately maculate with nearest RHS 59B; calyx between RHS 189A and RHS N187C;

Inflorescence: To about 28.0 cm tall from first branch and about 34.0 cm across; up to about 1,500 flowers per inflorescence;

Petals: Typically five, rarely four; broadly-lanceolate; acute apex; base truncate and fused; margin entire; glabrous abaxial and adaxial; average about 5.5 mm long and about 2.5 mm across at fusion;

Petal color: Adaxial nearest RHS 49D with irregular blotches lighter than RHS 59D; abaxial nearest N187D with irregular blotches of nearest RHS 55D; adaxial maturing to nearest RHS 56D along margins and nearest RHS 54C along the longitudinal center and eventually to nearest RHS NN155C to RHS NN155D; abaxial maturing to nearest RHS 54D in longitudinal center and between RHS 62D and RHS 56D along margins;

Calyx: With five sepals; campanulate to stellate; about 4.5 mm across and 3.0 mm deep;

Sepals: Linear to lanceolate; narrowly acute apex; fused base; entire margin; glabrous and slightly glaucous both abaxial and adaxial; adpressed to petals, about 2.5 mm long and about 1.0 mm across;

Sepal color: Abaxial and adaxial nearest RHS 191A blushed with N187C;

Peduncles: Terete; glaucous, glabrous; stiff and flexible; freely branching; mostly upwardly to slightly outwardly; with branches to about 45° from perpendicular; about 30.0 cm long and 6.0 mm diameter;

Peduncle color: Nearest RHS N 187C;

Pedicels: Cylindrical; glabrous; glaucous; strong and stiff, yet flexible; to about 7.0 mm long and 0.7 mm diameter; average about 4.5 mm long and 0.7 mm diameter;

Pedicel color: Blend between RHS N138D and RHS 186C;

Androecium: Typically ten stamens;

*Filaments*.—Cylindrical; outwardly; alternately free to fused to inner corolla in basal 1.0 mm; about 4.0 mm long and about 0.3 mm diameter; color between RHS 155B and RHS 56D.

*Anthers*.—Basifixed; longitudinal; ellipsoidal; about 0.7 mm long and 0.5 mm diameter; color nearest RHS 8D.

*Pollen*.—Moderate in quantity; color nearest RHS 8C.

Gynoecium: Typically five; cylindrical, conic in distal one third; about 5.5 mm long and 1.2 mm diameter;

*Style*.—Terete; ellipsoidal, tapering distally and base truncate; about 2.0 mm long and 0.5 mm diameter at point of attachment to ovary; glabrous; lustrous; color between RHS 61C and RHS 63A.

*Stigma*.—Minute, acute; about 0.2 mm diameter and 0.2 mm long; color nearest RHS 61C.

*Ovary*.—Nearly terete, acutely tapering at apex to style; base truncate; lustrous; about 2.0 mm long and 1.2 mm diameter; color nearest RHS 63B, developing with maturity to between RHS 63A and RHS 61A.

Fruit: Ventrally dehiscent follicle; about 3.5 mm long and 3.2 mm across; color at maturity nearest RHS 177A;

Seed: Sparse; fine; lanceolate; about 1.0 mm long and less than 0.2 mm across; color between RHS 165A and RHS 165B;

Growing conditions: Plants of the new *Sedum* 'Back in Black' is xeromorphic and grow best with good drainage, full sun and moderate to low fertility. The new plant is cold hardy from USDA zones 3 to 9 and has tolerated temperatures of at least 35 degrees C. 'Back in Black' tolerates heavy rains and wind and is not prone to develop an open center later in the season as many other *Sedum* cultivars do that are known to the inventor.

Disease and pest resistance: Other pest and disease resistance and tolerance outside that normal for *Sedum* is not known.

It is claimed:

1. A new and distinct perennial *Sedum* plant named 'Back in Black' as herein described and illustrated.

* * * * *